United States Patent
Guggenheimer et al.

(10) Patent No.: US 10,292,721 B2
(45) Date of Patent: May 21, 2019

(54) TISSUE-REMOVING CATHETER INCLUDING MOVABLE DISTAL TIP

(71) Applicant: Covidien LP, Mansfield, MA (US)

(72) Inventors: Ethan Guggenheimer, Minnetonka, MN (US); Benjamin Fruland, Blaine, MN (US); Lucas Schneider, Champlin, MN (US); Zachary Garvey, Stillwater, MN (US); Cory Sills, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 565 days.

(21) Appl. No.: 14/803,703

(22) Filed: Jul. 20, 2015

(65) Prior Publication Data

US 2017/0020539 A1 Jan. 26, 2017

(51) Int. Cl.
*A61B 17/22* (2006.01)
*A61B 17/3207* (2006.01)
*A61B 17/32* (2006.01)

(52) U.S. Cl.
CPC .......... *A61B 17/22* (2013.01); *A61B 17/3207* (2013.01); *A61B 17/320758* (2013.01); *A61B 17/320783* (2013.01); *A61B 2017/22038* (2013.01); *A61B 2017/22039* (2013.01); *A61B 2017/22045* (2013.01); *A61B 2017/320004* (2013.01); *A61B 2017/320064* (2013.01); *A61B 2017/320775* (2013.01); *A61B 2017/320791* (2013.01)

(58) Field of Classification Search
CPC ............ A61B 17/22; A61B 17/320783; A61B 2017/320791
See application file for complete search history.

(56) References Cited

U.S. PATENT DOCUMENTS

| | | | |
|---|---|---|---|
| 1,481,078 A | 1/1924 | Albertson |
| 2,178,790 A | 11/1939 | Henry |
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |

(Continued)

FOREIGN PATENT DOCUMENTS

| CA | 2000621 | 4/1990 |
|---|---|---|
| DE | 3732236 C1 | 12/1988 |

(Continued)

OTHER PUBLICATIONS

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

(Continued)

*Primary Examiner* — Ashley L Fishback

(57) ABSTRACT

A catheter includes a tissue-removing element and a tissue-containment chamber configured to receive tissue removed by the tissue-removing element. The tissue-containment chamber has a tissue-removing opening for use in removing tissue from the chamber. A closure component is associated with the tissue-removing opening for selectively opening and closing the opening.

24 Claims, 20 Drawing Sheets

(56) References Cited

U.S. PATENT DOCUMENTS

| | | |
|---|---|---|
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | Desatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMichael et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischeil |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |

(56) References Cited

U.S. PATENT DOCUMENTS

| | | |
|---|---|---|
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jung |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |

(56) References Cited

U.S. PATENT DOCUMENTS

| | | |
|---|---|---|
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wislon et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |

(56) References Cited

U.S. PATENT DOCUMENTS

| | | |
|---|---|---|
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,192,452 B2 | 6/2012 | Moberg |
| 8,574,249 B2 | 11/2013 | Moberg |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |

(56) References Cited

U.S. PATENT DOCUMENTS

| | | |
|---|---|---|
| 2011/0040315 A1 | 2/2011 | To et al. |
| 2011/0130777 A1 | 6/2011 | Zhang et al. |
| 2011/0144673 A1 | 6/2011 | Zhang et al. |
| 2011/0152841 A1* | 6/2011 | Nemoto ............ A61M 39/26 604/533 |
| 2014/0222044 A1 | 8/2014 | Ladd et al. |
| 2015/0057690 A1 | 2/2015 | Simpson et al. |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |

OTHER PUBLICATIONS

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).
International Search Report and Written Opinion for PCT Application No. PCT/US2016/043103, dated Oct. 12, 2016, 16 pages.
Brezinski et al., "Optical Coherence Tomography for Optical Biopsy," Circulation, 93:1206-1213 (1996).
Brezinski et al., "Assessing Atherosclerotic Plaque Morphology: Comparison of Optical Coherence Tomography and High Frequency Intravascular Ultrasound," Heart, 77:397-403 (1997).
Huang et al., "Optical Coherence Tomography," Science, 254:1178-1181 (1991).

* cited by examiner

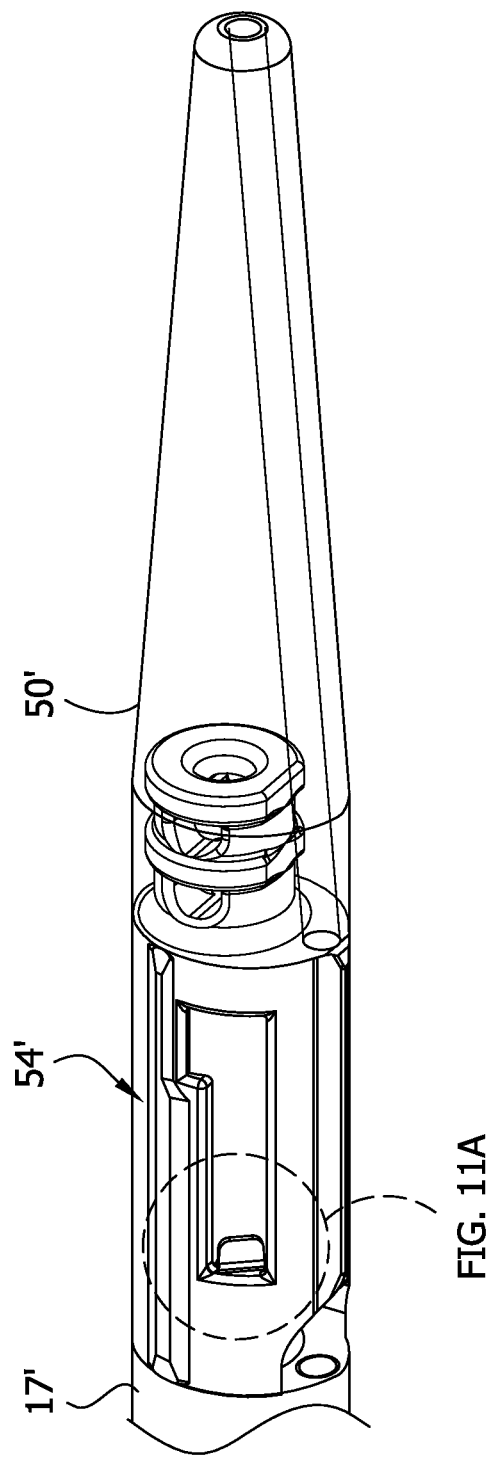

US 10,292,721 B2

TISSUE-REMOVING CATHETER INCLUDING MOVABLE DISTAL TIP

FIELD OF THE DISCLOSURE

The present disclosure generally relates to a tissue-removing catheter including a moveable distal tip, and more particularly a moveable distal tip that enables on wire tissue cleaning.

BACKGROUND OF THE DISCLOSURE

Debulking or tissue-removing catheters are used to remove unwanted tissue from the body. As an example, atherectomy catheters are used to remove material from a blood vessel to open the blood vessel and improve blood flow through the vessel. An atherectomy catheter may be advanced over a guide wire which extends through a guide wire lumen of the catheter to facilitate insertion of the catheter though the vessel. Current atherectomy catheters may require removal of the guide wire from the guide wire lumen to clean the catheter.

SUMMARY OF THE DISCLOSURE

In one aspect, a catheter includes a tissue-removing element and a tissue-containment chamber configured to receive tissue removed by the tissue-removing element. The tissue-containment chamber has a tissue-removing opening for use in removing tissue from the chamber. A closure component is associated with the tissue-removing opening for selectively opening and closing the opening. Embodiments of the tissue-containment chamber and the closure component facilitate removal of tissue from the tissue-containment chamber.

Other features will be in part apparent and in part pointed out hereinafter.

BRIEF DESCRIPTION OF THE DRAWINGS

FIG. 11 is another illustration of the catheter of FIG. 6 showing a stop;

Corresponding reference characters indicate corresponding parts throughout the drawings.

DETAILED DESCRIPTION OF THE DISCLOSURE

Embodiments of a tissue-removing catheter having moveable distal portions for removing material stored in the catheter are disclosed. In particular, the illustrated catheter embodiments are particularly suitable for removing (i.e., excising) plaque tissue from a blood vessel (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory channels, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from, and penetrating occlusions in, blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 1:
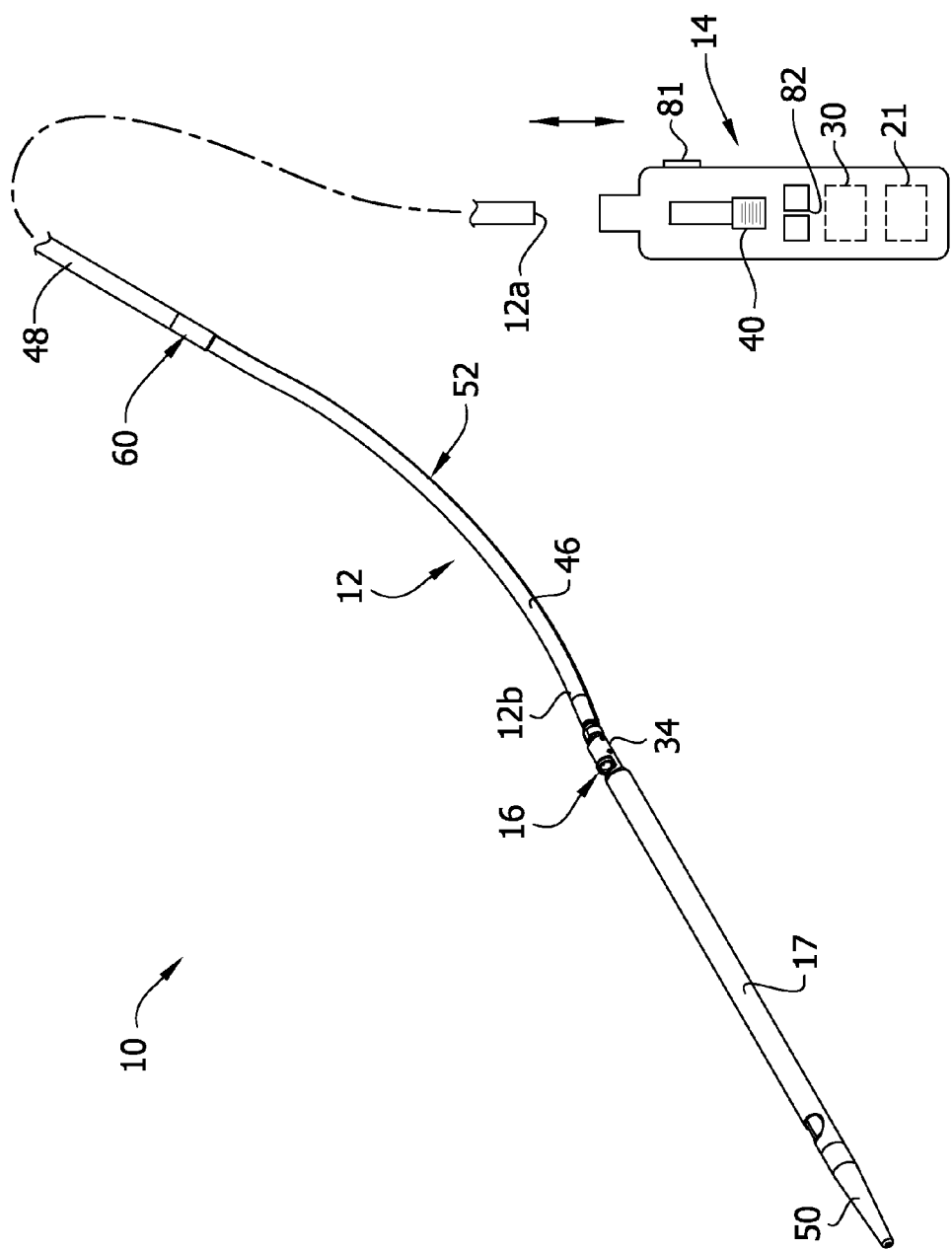
FIG. 1 is a perspective of a catheter and a schematic representation of a handle, each of which are part of a catheter.

Referring to FIG. 1, a tissue-removing catheter, in accordance with one or more embodiments of the present disclosure, is generally indicated at reference numeral 10. The catheter 10 comprises an elongate catheter body, generally indicated at 12, having opposite proximal and distal ends 12a, 12b, respectively, and a longitudinal axis extending between the proximal and distal ends. The catheter body 12 can have other configurations without departing from the scope of this disclosure. A handle or control unit, generally indicated at 14, is disposed on the proximal end 12a of the catheter body 12 for manipulation by a user. A tissue-removing element, generally indicated at 16, generally adjacent the distal end 12b of the catheter body 12, is configured to remove (e.g., cut) tissue from the body lumen and direct the removed tissue into a lumen 15 (FIG. 2) of a tissue-containment chamber 17 adjacent the distal end of the catheter body. The catheter 10 is advanced over a guide wire 18 which extends through a guide wire lumen 19 on the catheter (FIG. 3). The guide wire 18 facilitates manipulation of the catheter 10 through the subject's blood vessels.

Figure 2:
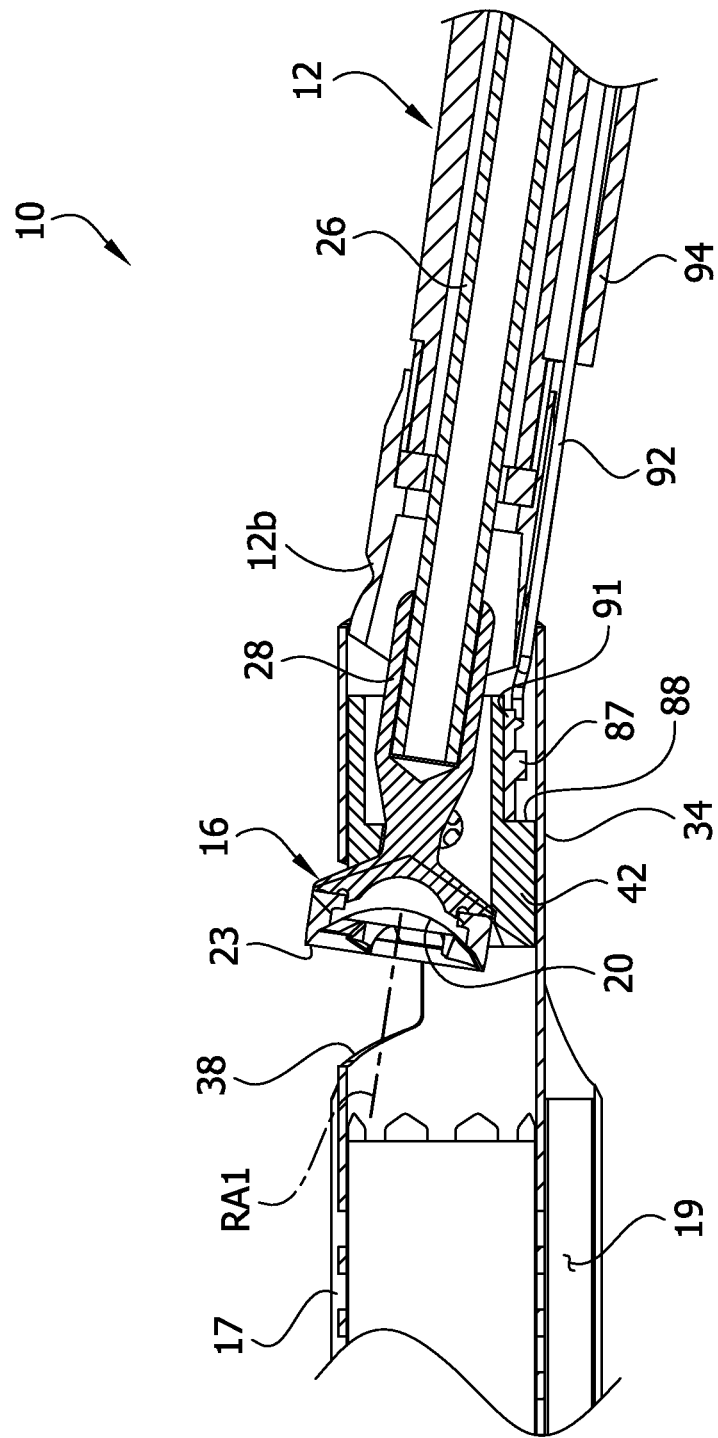
FIG. 2 is an enlarged fragmentary cross section of the catheter including a tissue-containment chamber, and illustrating a tissue-removing element of the catheter in a deployed position.
Figure 3:
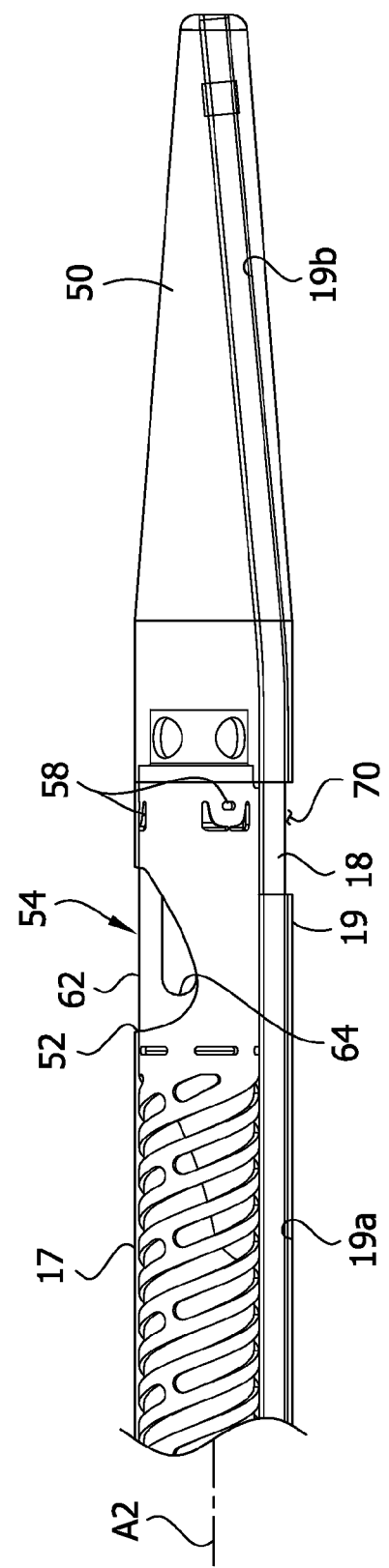
FIG. 3 is an illustration of a distal end of the catheter showing the catheter in a closed position and with the tissue containment chamber and distal end shown as transparent showing internal detail.

Referring to FIG. 2, in the illustrated embodiment, the tissue-removing element 16 comprises a rotatable cutting element that is rotatable about a rotation axis RA1 for cutting tissue. The illustrated cutting element 16 has a cutting edge 23 facing distally, although in other embodiments the cutting edge may face proximally, and a cup-shaped surface 20 for directing removed tissue distally into the tissue-containment chamber 17 of the catheter body 12. In other embodiments, the tissue-removing element may have other configurations for cutting tissue, or may be configured to remove tissue in other ways. For example, the tissue-removing element may be configured to ablate tissue, or abrade tissue, or otherwise remove tissue from the body lumen. Moreover, the tissue-removing element may not be rotatable relative to the catheter body.

Referring still to FIG. 2, a tissue-removing driveshaft 26 is operatively connected to a stem 28 of the tissue-removing element 16 (e.g., fixedly secured thereto) for imparting rotation to the tissue-removing element. The tissue-removing driveshaft 26 (e.g., a coiled driveshaft) extends through the catheter body 12 and is operatively connectable to an electric driveshaft motor 30 (FIG. 1), or other prime mover, in the handle 14 for driving rotation of the driveshaft, and in turn, driving rotation of the tissue-removing element 16, relative to the catheter body. The driveshaft motor 30 is electrically connected to a power source 21 in the handle 14 (FIG. 1). In the illustrated embodiment, the driveshaft 26 is movable longitudinally within the catheter body 12 to impart longitudinal movement of the tissue-removing element 16 relative to the catheter body. Longitudinal movement of the tissue-removing element 16 actuates deployment and storage of the tissue-removing element relative to a tissue-removing housing 34, which is connected to the distal end 12b of the body 12. A distal portion of the housing 34 forms the tissue container 17, although the housing and the tissue collection chamber may be formed separately.

The tissue-removing element 16 is movable between a stored position (not shown) and a deployed position (FIGS. 1 and 2). In the stored position, the tissue-removing element 16 is received in the housing 34 and is not exposed through a window or side opening 38 of the housing. To deploy the tissue-removing element 16, the driveshaft 26 is moved proximally relative to the catheter body 12, such as by moving a lever or other actuator 40 (FIG. 1) on the handle 14 that is operatively connected to the driveshaft, to impart proximal movement of the tissue-removing element 16 relative to the housing 34. Referring to FIG. 2, as the tissue-removing element 16 moves proximally, the tissue-removing element, which acts as a cam, engages and moves longitudinally along an internal cam follower 42 of the housing 34, causing the housing to pivot or deflect relative to the body 12 and the tissue-removing element to extend partially out of the window 38. To return the tissue-removing element 16 to its stored, non-deployed position, the driveshaft 26 is moved distally, such as by moving the actuator 40 distally, to impart distal movement of the tissue-removing element 16 along the cam follower 42. Distal movement of the tissue-removing element 16 causes the housing 34 to pivot or deflect back relative to the body 12 so that the tissue-removing element is received in the housing 34 and does not extend outside the window 38. When the tissue-removing element 16 is in its stored position, the driveshaft motor 30 is deactivated (i.e., turned off). It is understood that a catheter 10 constructed according to the principles of the present disclosure may not include a deployment mechanism (e.g., the tissue-removing element or other functional element may always be deployed or may remain within the catheter body).

The material cut by the tissue-removing element 16 is directed through the window 38 and into the lumen 15 of the tissue-containment chamber 17 located distal to the window. The catheter 10 may be passed through the vessel a number of times with the material from each pass being stored in the tissue-containment chamber 17. When the tissue-containment chamber 17 is full, the catheter 10 is removed from the patient and the tissue-containment chamber may be cleaned for subsequent use as described below.

Figure 4:
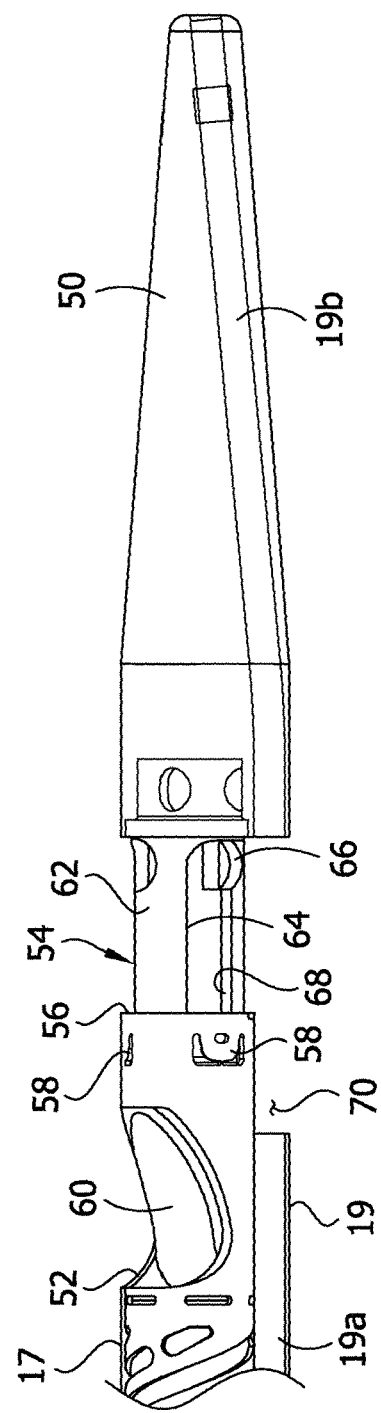
FIG. 4 is an illustration of the distal end of the catheter showing the catheter in an open position and with the tissue containment chamber and distal end shown as transparent showing internal detail.

Referring now to FIGS. 3 and 4, a distal tip component 50 is disposed at the distal end of the tissue-containment chamber 17. The distal tip component 50 may be formed from a flexible material such that the tip component is generally atraumatic. The tissue-containment chamber 17 defines a tissue-removing opening 52 to facilitate removal of the material from the chamber. The tissue-removing opening 52 is selectively opened and closed by movement of a closure component, generally indicated at 54. The closure component 54 has a proximal end received in a distal opening 56 of the tissue-containment chamber 17, and a distal end attached to a proximal end of the distal tip component 50. Movement of the distal tip component 50 causes conjoint movement of the closure component 54 in the lumen 15 of the tissue containment chamber 17. In particular, the distal tip component 50 and closure component 54 are slidable along a longitudinal axis A2 of the tissue-containment chamber 17 to move between a closed position of FIG. 3, where the tissue-removing opening 52 is blocked by the closure component (i.e., closed), and an open position of FIG. 4, where the tissue-removing opening is unblocked (i.e., open). For reasons explained below, the tissue-containment chamber 17 has a plurality of tabs 58 (broadly, one or more bosses) disposed near a distal end of the tissue-containment chamber. The tabs 58 extend into the lumen 15 of the tissue-containment chamber 17. In the illustrated embodiment, the tabs 58 are punched from the tissue-containment chamber 17. The tabs 58 can have other configurations and can be formed in other ways without departing from the scope of the disclosure. For instance the tabs 58 can be formed separately from the tissue-containment chamber and suitably attached to the tissue-containment chamber 17.

In the illustrated embodiment, as shown in FIG. 4, the closure component 54 includes an elongate body having a scoop portion 60 at its proximal end that is curved to direct material out of the tissue-removing opening 52 when in the open position. As shown in FIG. 3, a plug portion 62 of the body blocks the tissue-removing opening 52 in the tissue-containment chamber 17 when the closure component 54 is in the closed position. The closure component 54 may have other constructions without departing from various aspects of the present disclosure. For example, the scoop portion 60 of the closure component 54 could have a conical shape, or other shapes, with multiple openings to allow expungement in multiple directions. Moreover, the scoop portion 60 may be omitted in other embodiments.

Figure 5:
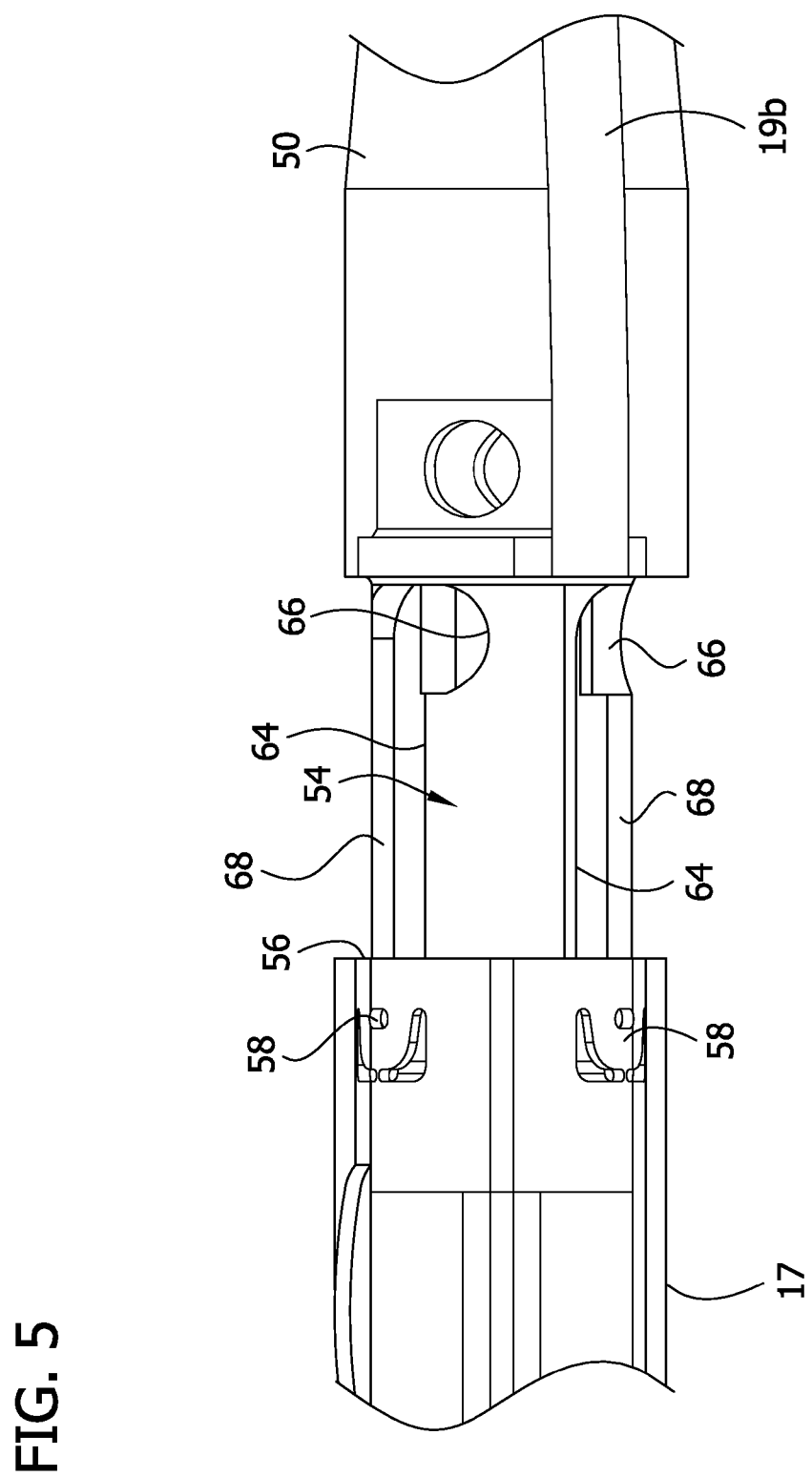
FIG. 5 is another illustration of the distal end of the catheter showing the catheter in the open position and with the tissue containment chamber and distal end shown as transparent showing internal detail.

The closure component 54 includes a plurality of L-shaped slots 64 (broadly, one or more grooves) each having a circumferentially extending portion 66, an axially extending portion 68, and a juncture connecting the axially extending portion to the circumferentially extending portion. Only one L-shaped slot 64 is visible in FIGS. 3 and 4, and two L-shaped slots are visible in FIG. 5. As shown in FIGS. 4 and 5, the circumferentially extending portion 66 of each slot 64 is disposed near the distal end of the closure component 54, and the axially extending portion 68 extends from the juncture toward the proximal end of the closure component. In one embodiment, each of the circumferentially extending portions 66 subtends about 30° about a circumference of the closure component 54. In another embodiment, each of the circumferentially extending portions 66 subtends between about 15° and about 45° about the circumference of the closure component 54. The tabs 58 of the tissue-containment chamber 17 are retained in respective L-shaped slots 64 to form a boss-and-groove connection. The tabs 58 are moveable within the slots 64 to permit movement of the closure component 54 relative to the tissue-containment chamber 17 between the open and closed positions. The slots 64 may have other configurations than L-shaped. For instance, slots (not shown) may be U-shaped to allow circumferential movement of the tabs in the slots in both clockwise and counterclockwise directions prior to sliding the tabs axially in one of the legs of the U-shaped slots. Alternatively, the slots (not shown) may be J-shaped.

To move the closure component 54 from the closed position (FIG. 3) to the open position (FIG. 4), the distal tip component 50 may be grasped and rotated counterclockwise (as viewed from the distal end of the tip 50) so the tabs track in the circumferentially extending portions 66 and into the junctures between the circumferentially extending portions and the longitudinally extending portions 68. Rotating the closure component 54 in this manner generally axially aligns the scoop portion 60 of the closure component with the tissue-removing opening 52 in the tissue-containment chamber 17. The distal tip component 50 may then be moved in an axial direction (e.g., distally) to slide the closure component 54 axially (e.g., distally) so that the tabs 58 track along the axially extending portions 68 of the slots 64. The axial movement of the distal tip component 50 may be aided by a spring (not shown) disposed between the tissue-containment chamber 17 and the distal tip component 50. The sliding engagements between the slots 64 and tabs 58 also prevent the distal tip component 50 and closure component 54 from being separated from the tissue-containment chamber 17. The distal tip component 50 is moved until the scoop portion 60 of the closure component 54 is positioned in registration with the tissue-removing opening 52 in the tissue-containment chamber 17, thereby opening the tissue-removing opening. In this position, the tabs 58 engage the end (e.g., proximal end) of the axially extending portions 68 of the slots 64 to inhibit further axial movement of the closure component 54. Once the tissue-removing opening 52 has been opened, material in the tissue-containment chamber 17 may be removed in a number of different ways. The material may simply be discarded in the appropriate manner after removal from the catheter 10. Alternatively, the material may also be saved in a storage container (not shown). It will be understood that the tabs 58 may be on the closure component 54 and the slots 64 may be in the tissue-containment chamber 17 without departing from the scope of the disclosure. Also, any number of tabs 58 and slots 64 can be incorporated without departing from the scope of the disclosure.

The guide wire lumen 19 extends along the catheter 10 and includes a proximal section 19*a* extending along (e.g., mounted on) the tissue-containment chamber 17 and a distal section 19*b* extending along (e.g., mounted on) the distal tip component 50. The proximal and distal sections 19*a*, 19*b* of the guide wire lumen 19 are spaced apart by a gap or void 70. The proximal section 19*a* of the guide wire lumen 19 is aligned with the distal section 19*b* when the closure component 54 is in the closed position of FIG. 3. In this manner, when the closure component 54 is in the closed position and the guide wire 18 is fully inserted into the guide wire lumen 19, the guide wire 18 inhibits unintentional rotation of the closure component, thereby maintaining or locking the closure component in the closed position. The guide wire 18 may lock the closure component in other suitable ways to inhibit unintentional opening of the tissue-removing opening 52. For example, the catheter may include a biased locking element (not shown).

The construction of the tissue-containment chamber 17 and closure component 54 permit rotation and axial sliding of the distal tip component 50 to expose the tissue-removing opening 52 without having to remove the guide wire 18 from either of the sections 19*a*, 19*b* of the guide wire lumen 19. When the rotational force is applied to the distal tip component 50, the closure component 54 rotates and the tabs 58 on the tissue containment chamber 17 track in the circumferentially extending portions 68 of the slots 64 in the closure component and into the juncture. Rotating the distal tip component 50 applies bending stress to the guide wire 18 because proximal and distal portions 19*a*, 19*b* of the guide wire lumen 19 become unaligned. The guide wire resiliently bends under the applied bending stress and stores a return force biasing the closure component 54 to the closed position. As a result, the return force in the guide wire 18 can automatically move the closure component 54 to the closed position when the tabs 58 are located at the junctures and the rotational force applied by the user is removed. However, if the rotational force is maintained by the user, the distal tip component 50 can then be pulled distally, and/or urged distally by a stored energy component (e.g., spring) to move the closure component 54 distally and track the tabs 58 on the tissue-containment chamber 17 in the axially extending portions 68 of the slots 64 in the closure component 54 to open the tissue-removing opening 52. With the tabs 58 received in the axially extending portions 68 of the slots 64, the return force being generated by the guide wire 18 acts to hold the closure component 54 in the open position. This reduces the chance of the closure component 54 sliding back into the closed position. When the catheter 10 is removed from the patient, the guide wire 18 remains in the guide wire lumen 19. By leaving the guide wire 18 in the guide wire lumen 19, cleaning the catheter 10 is more efficient than having to remove the guide wire before cleaning and then reinsert the guide wire into the guide wire lumen after cleaning.

When it is desired to close the tissue-removing opening 52, the distal tip component 50 is pushed proximally to track the tabs 58 into the junctures between the axially extending portions 68 and the circumferentially extending portions 66 of the slots 64. The return force of the guide wire 18 may aid in or automatically move the closure component 54 back to the closed position, thereby closing the tissue-removing opening 52. Additionally, if the distal tip component 50 and closure component 54 are not moved to the closed position before the catheter 10 is used, a distal to proximal force acting on the distal tip component when the catheter is inserted into a hemostasis valve can move the closure component axially (e.g., proximally) to track the tabs 58 into the junctures so that the closure component moves to the closed position under the return force of the guide wire 18.

Additionally or alternatively, a snapping mechanism (not shown) may lock the distal tip component 50 and closure component 54 in the closed or open position. A small axial force may be necessary to unseat the snapping mechanism to move the distal tip component 50 and closure component 54 relative to the tissue-containment chamber 17. The snapping mechanism may comprise a metal to metal or metal interference fit or a metal to plastic interference fit to lock the distal tip component 50 and closure component 54 in the closed or open position.

Figure 6:
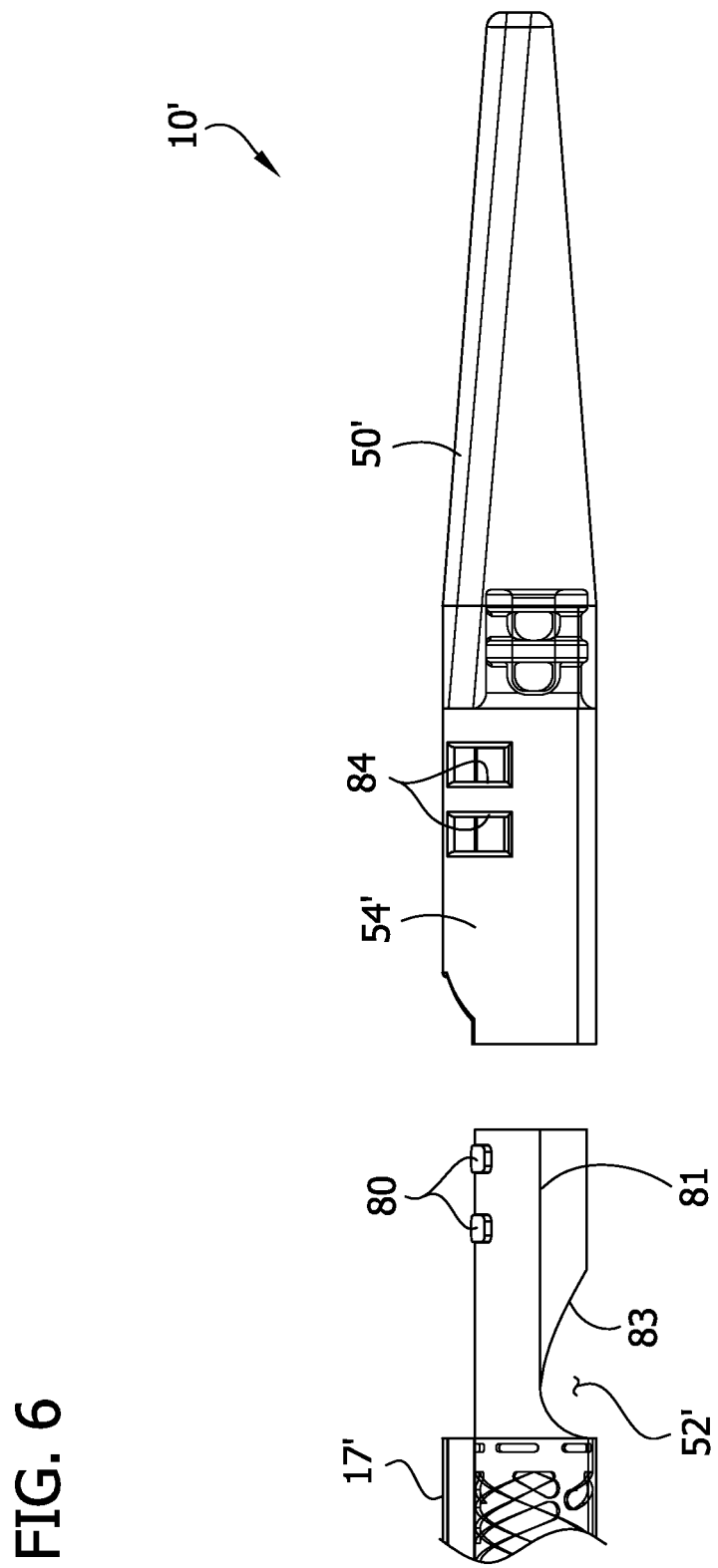
FIG. 6 is an illustration of a distal end of a catheter of another embodiment showing a distal tip component and closure component separated from a tissue-containment chamber and with the tissue containment chamber and distal tip component shown as transparent showing internal detail.
Figure 6A:
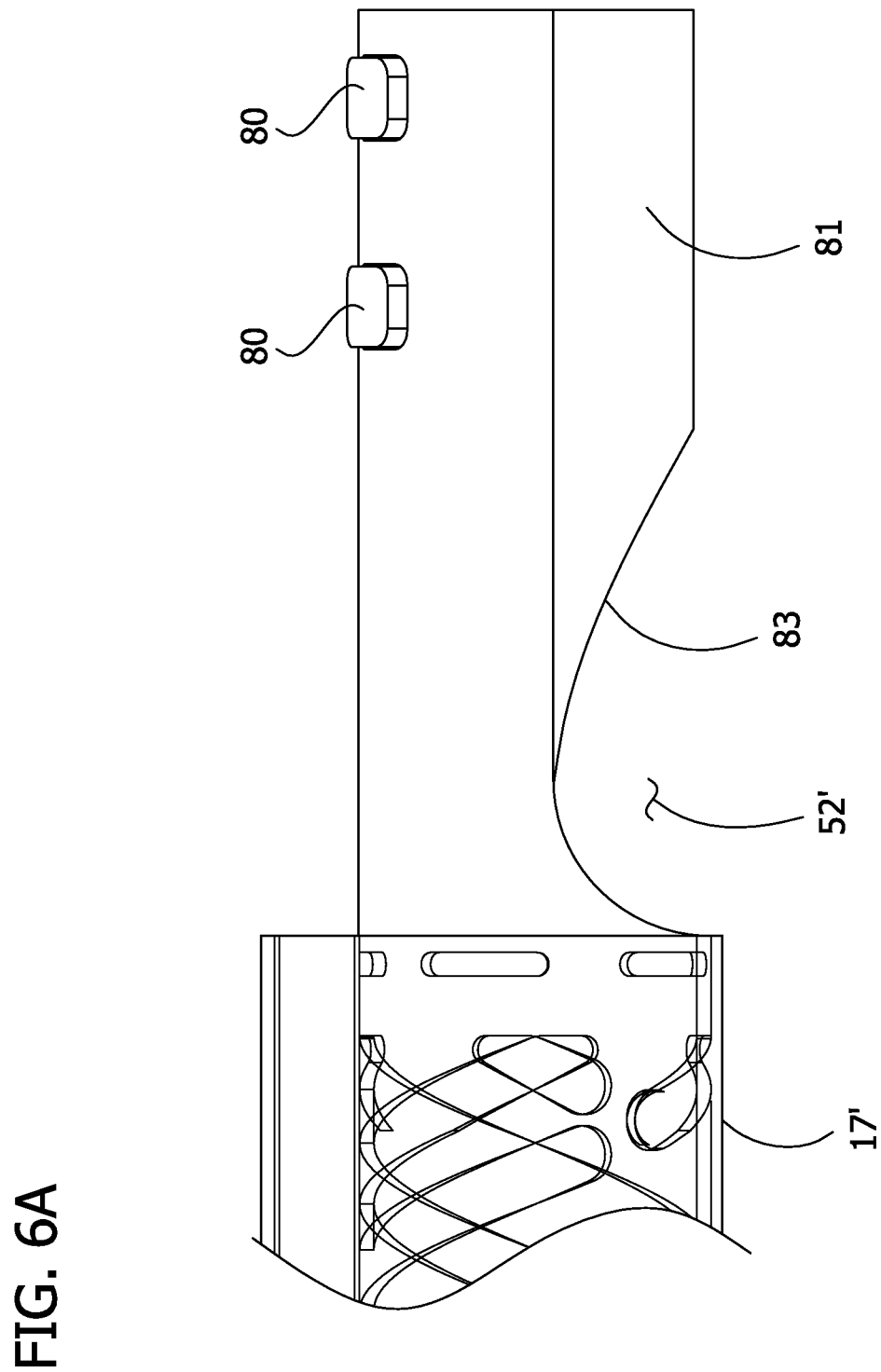
FIG. 6A is an enlarged fragmentary view of the tissue-containment chamber in FIG. 6.
Figure 6B:
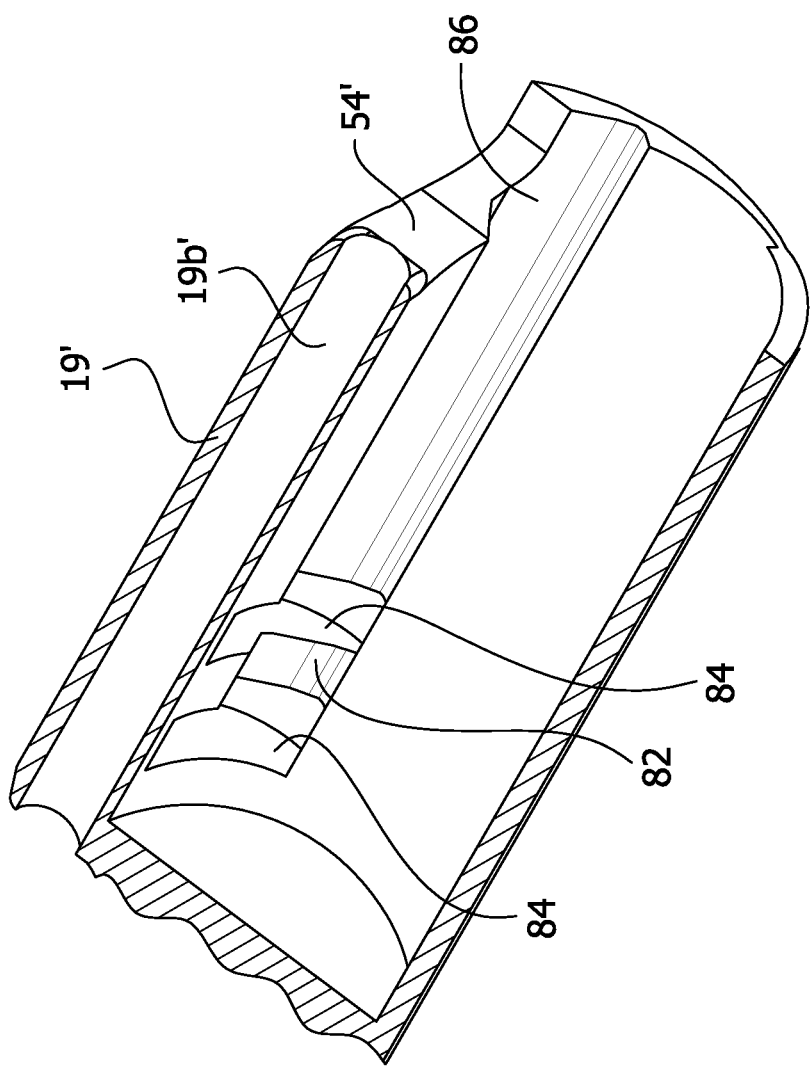
FIG. 6B is an enlarged fragmentary view of the closure component in FIG. 6 with portions removed showing interior detail.

Referring to FIG. 6-6B, a catheter 10' of another embodiment includes protrusions 80 (broadly, one or more bosses) formed on an extension member 81 of a tissue-containment chamber 17' near a distal end of the chamber, and a channel 82 (broadly, one or more grooves; FIG. 6B) formed in an interior surface of a closure component 54'. In the illustrated embodiment, the closure component 54' is slidably received on the extension member 81 such that the closure component functions as a sleeve. The extension member 81 defines a tissue-removing opening 52' of the tissue-containment chamber 17', which is generally in the form of a side opening. The tissue-removing opening 52' may be defined by a scoop portion of the extension member 81. A pair of protrusions 80 are axially aligned and spaced along the extension member 81 of the tissue-containment chamber 17'. The channel 82 includes a pair of circumferentially extending portions 84 axially aligned and spaced along the interior surface of the closure component 54', and an axially extending portion 86 extending between ends of the circumferentially extending portions 84 and proximally from the circumferentially extending portions. The protrusions 80 on the tissue-containment chamber 17' are retained in channel 82 to form a boss-and-groove connection. The protrusions 80 track within the channel 82 to guide the closure component 54' relative to the tissue-containment chamber 17' between open and closed positions.

Figure 7:
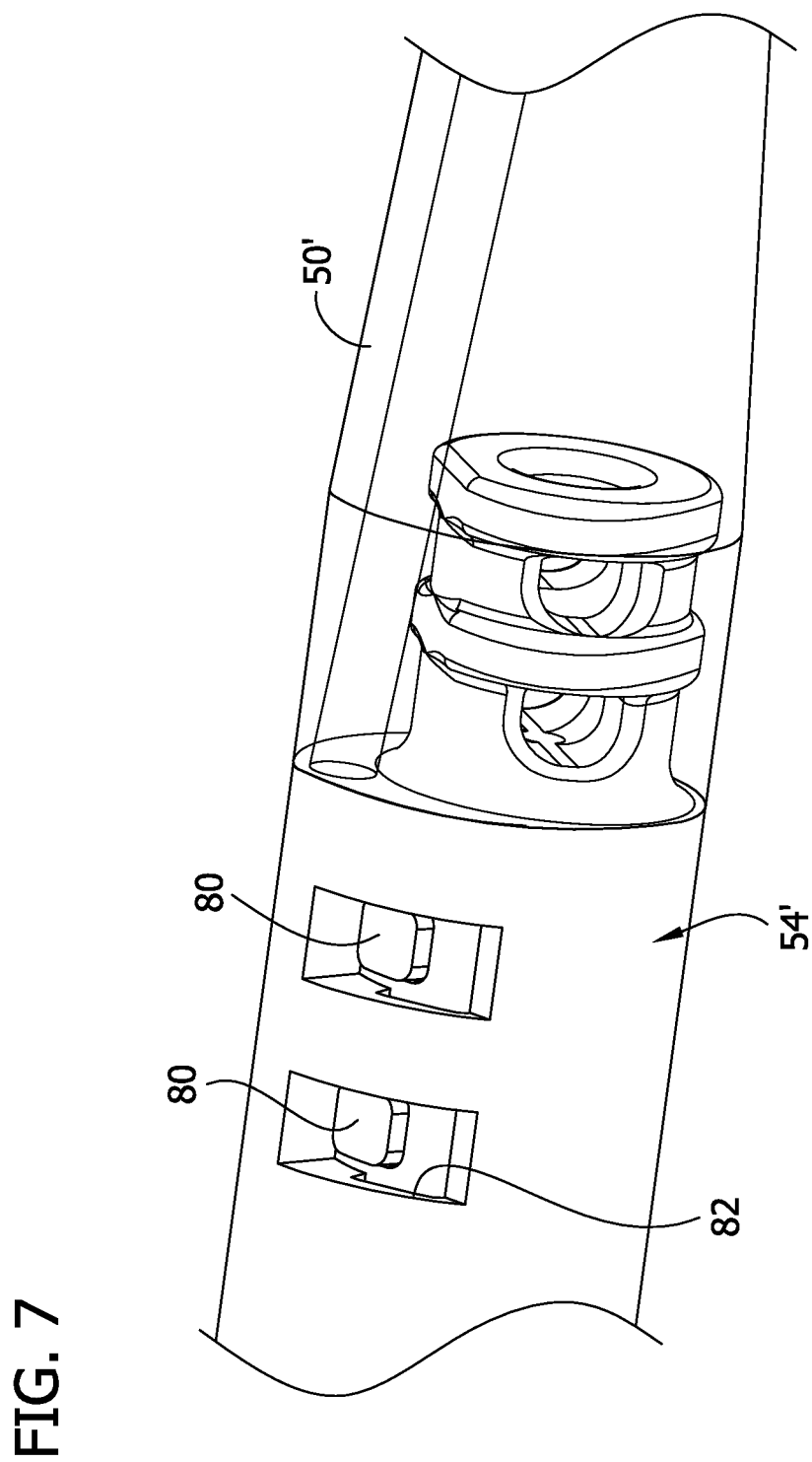
FIG. 7 is an illustration of the catheter of FIG. 6 showing the catheter in a closed and locked position.
Figure 7A:
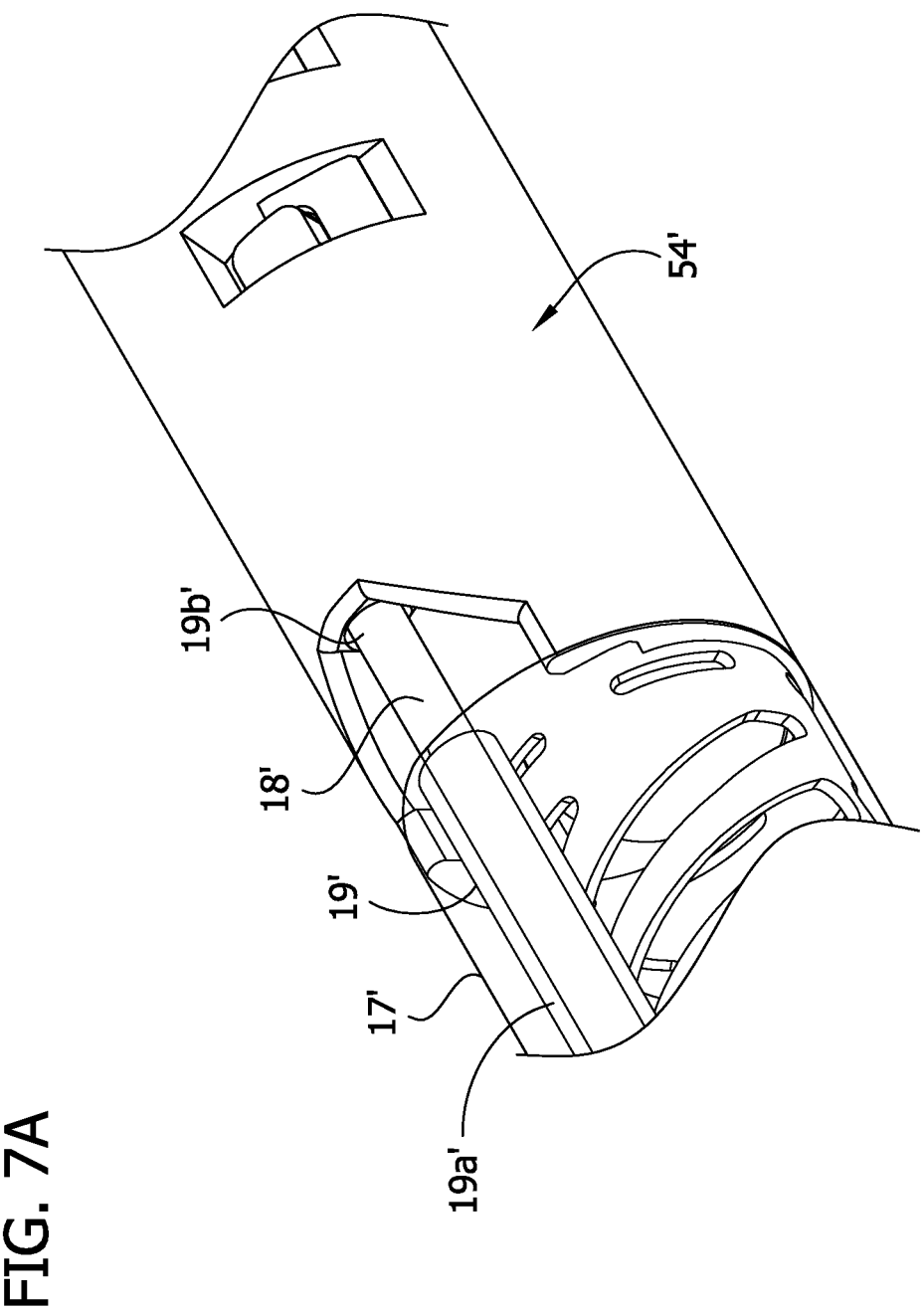
FIG. 7A is another illustration of the catheter of FIG. 6 showing the catheter in a closed and locked position.
Figure 8:
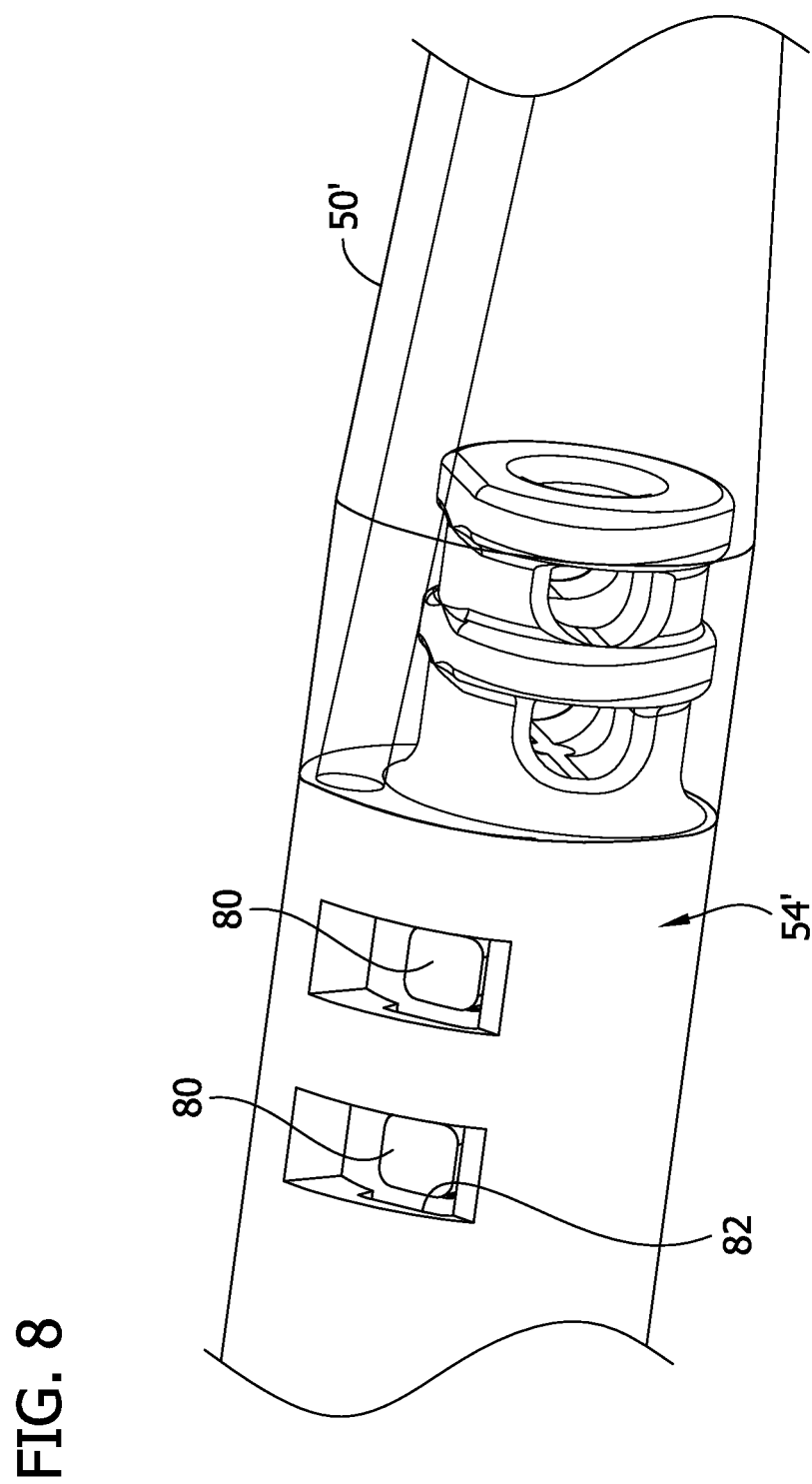
FIG. 8 is an illustration of the catheter of FIG. 6 showing the catheter in a closed position and unlocked.

To move the closure component 54' from a closed and locked position (FIGS. 7 and 7A), in which the closure component covers the tissue-removing opening 52', to an open position (FIGS. 9 and 10), a distal tip component 50' may be grasped and rotated counterclockwise (as viewed from the distal end of the tip component) to track each protrusion 80 in a respective circumferentially extending portion 84 of the channel 82 to the juncture between the circumferentially extending portion and the axially extending portion 86 of the channel, as shown in FIG. 8. As explained in the previous embodiment and shown in FIG. 8A, rotating the closure component 54' in this manner bends a guide wire 18' in the guide wire lumen 19, which places a return load on the guide wire for returning the catheter 10' to the closed position.

Figure 8A:
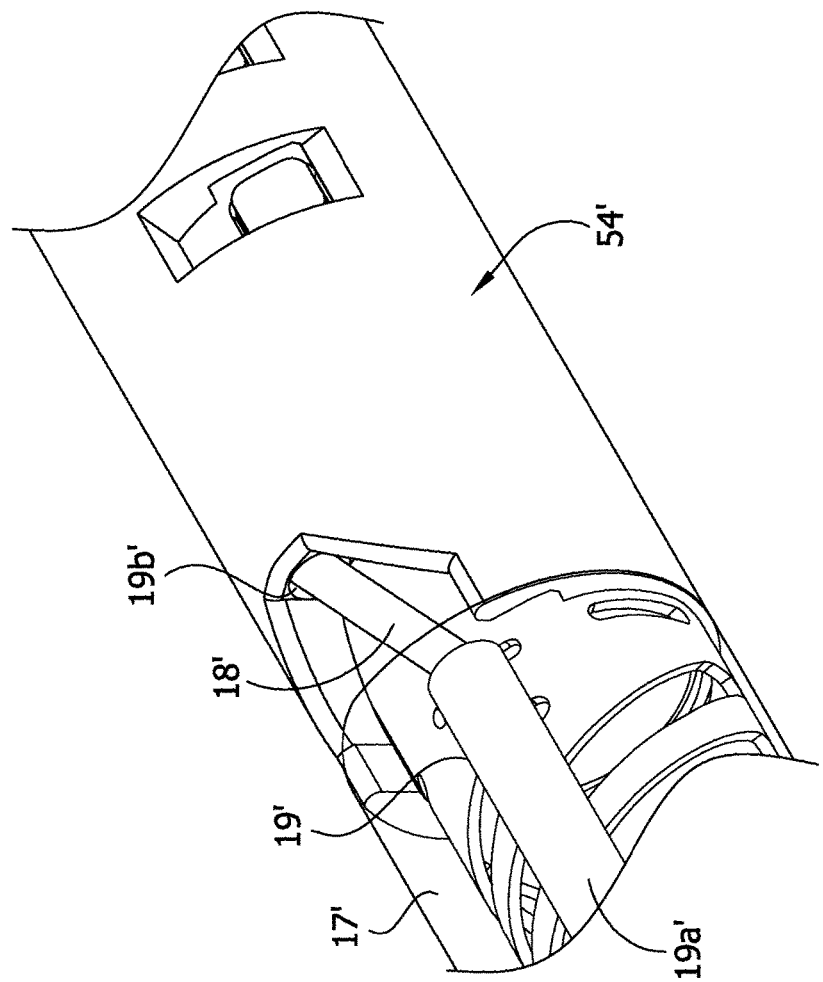
FIG. 8A is another illustration of the catheter of FIG. 6 showing the catheter in a closed position and unlocked.
Figure 9:
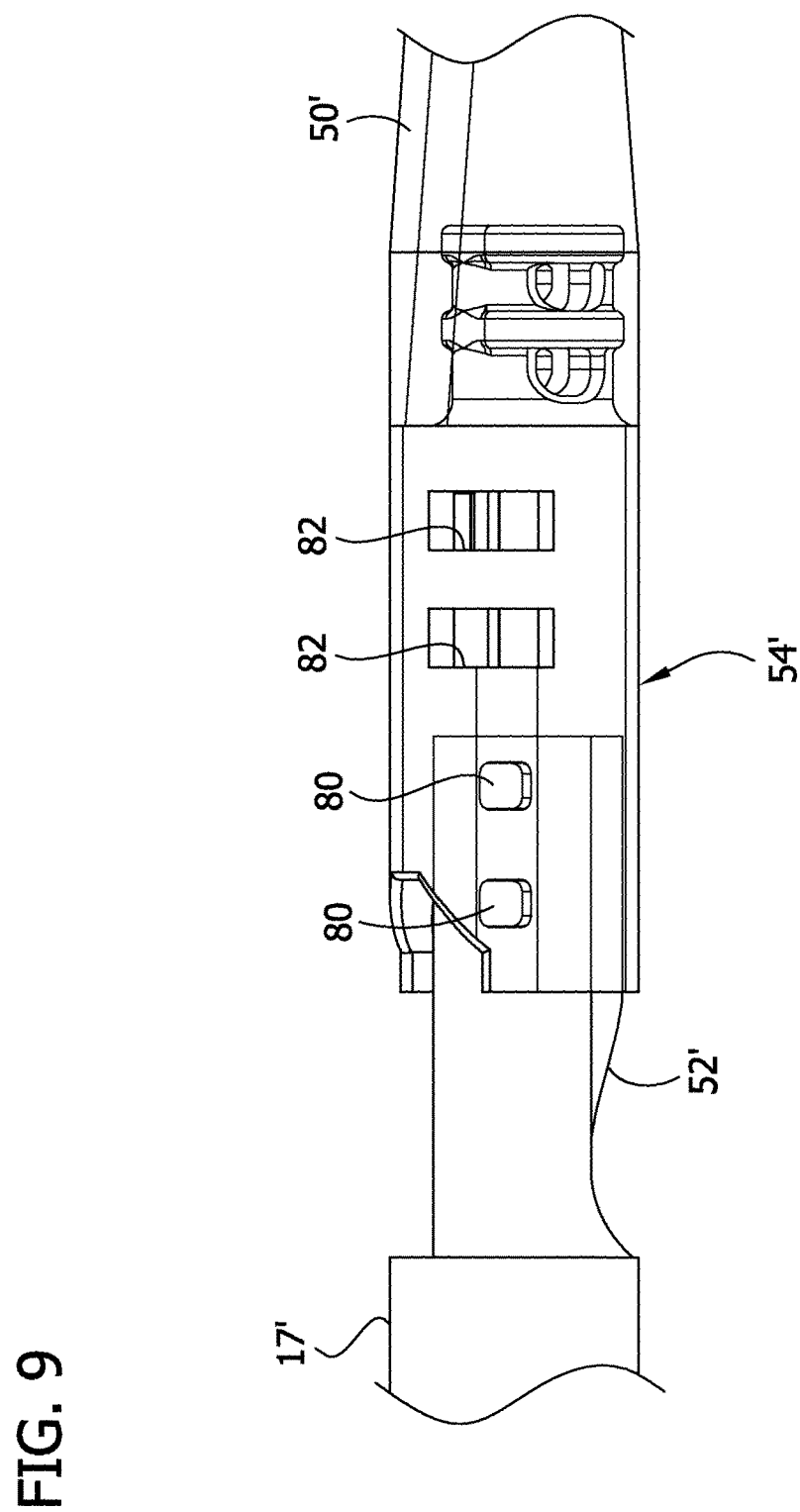
FIG. 9 is an illustration of the catheter of FIG. 6 showing the catheter in an open position.
Figure 10:
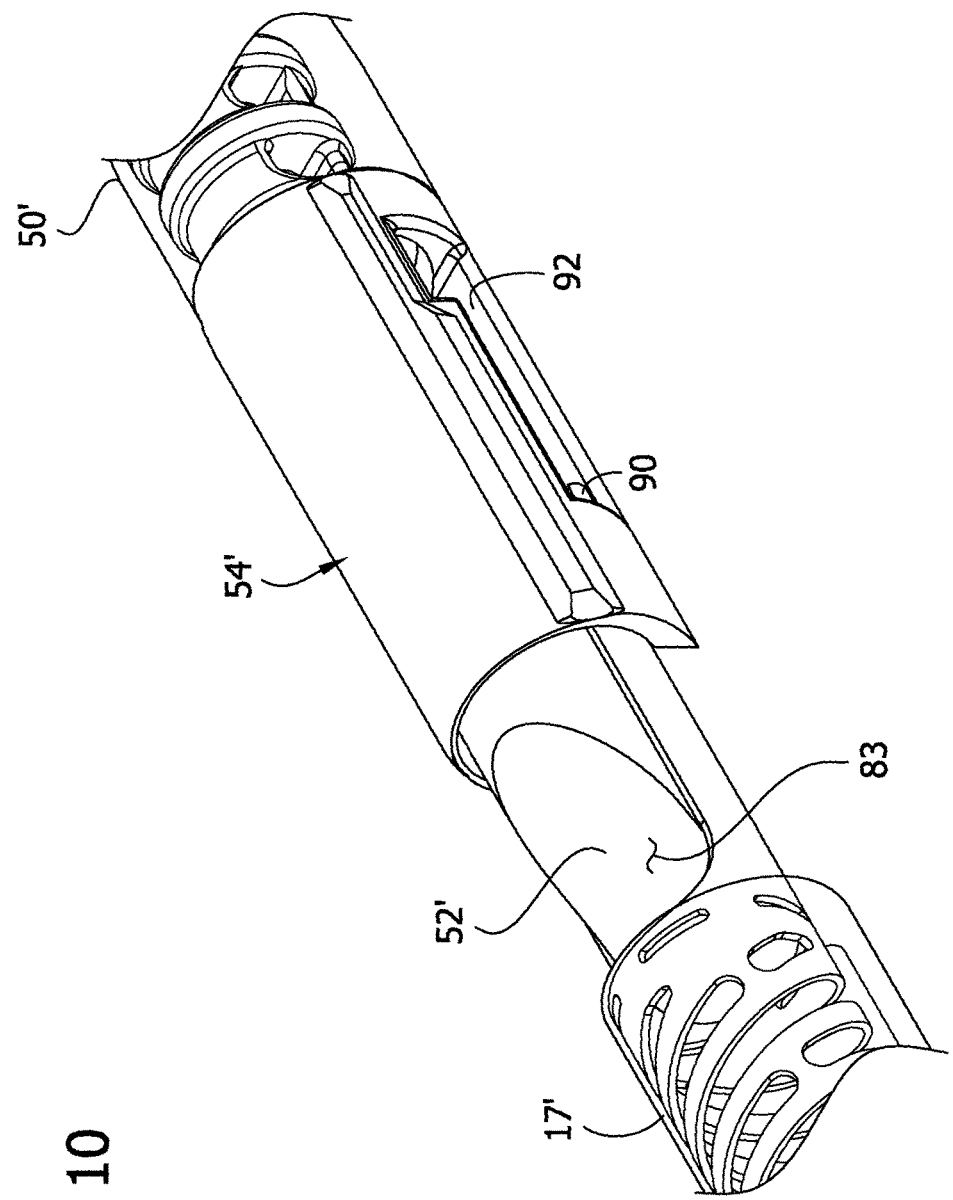
FIG. 10 is another illustration of the catheter of FIG. 6 showing the catheter in the open position.

From the rotational position shown in FIGS. 8 and 8A, the distal tip component 50' can then be moved in an axial direction to slide the protrusions 80 along the axially extending portion 86 of the channel 82. The distal tip component 50' is pulled until the closure component 54' no longer covers the tissue-removing opening 52' of the tissue-containment chamber 17' thereby opening the tissue-removing opening, as shown in FIGS. 9 and 10. It will be understood that the protrusions 80 may be on the closure component 54' and the channel 82 may be formed in the tissue-containment chamber 17' without departing from the scope of the disclosure.

Figure 11A:
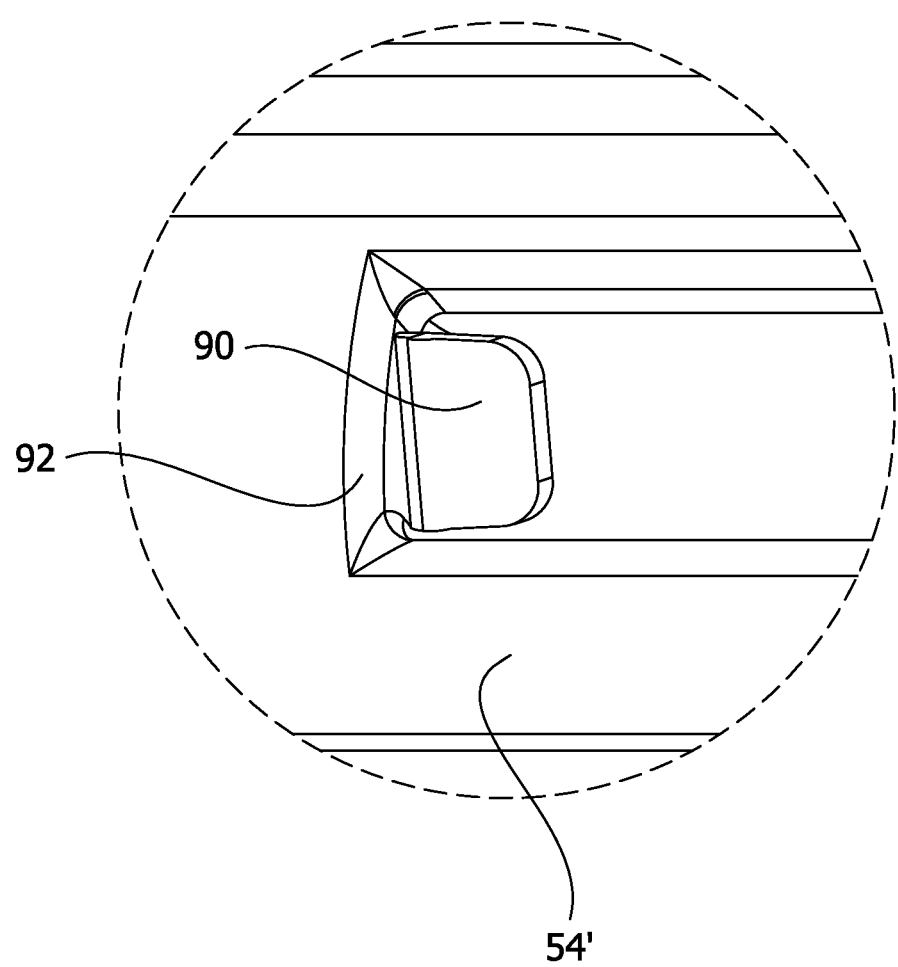
FIG. 11A is an enlarged fragmentary view of catheter of FIG. 11.

Referring to FIGS. 10, 11 and 11A, a stop 90 may be disposed near a distal end of the tissue-containment chamber 17' to limit movement of a closure component 54' distally away from the tissue-containment chamber. In the illustrated embodiment, the stop 90 comprises a tab attached to an outer surface of the tissue-containment chamber 17', more specifically the extension member 81 of the tissue-containment chamber. The tab 90 engages a proximal end of a slot 92 formed in the closure component 54' to limit further movement of the closure component. The stop 90 may engage some other portion of the catheter to limit movement of the closure component without departing from the scope of the disclosure.

Additionally or alternatively, tabs (not shown) can be machined into the closure component, and a slot (e.g., laser cut) may be formed in the tissue-containment chamber.

Additionally or alternatively, multiple laser cut tabs may be formed on the distal end of a tissue-containment chamber. A most proximal tab can lock a machined feature on a closure component until a distal tip component is pushed proximally against a gasket (not shown) and then rotated and pulled distally as described in previous embodiments. Movement of the distal tip component and closure component in the distal direction is stopped by a distal most tab on the tissue-containment chamber. Thus, the locking mechanism is built into the tabs rather than using the return force created between the guide wire and sections of the guide wire lumen when the closure component is rotated.

Figure 12:
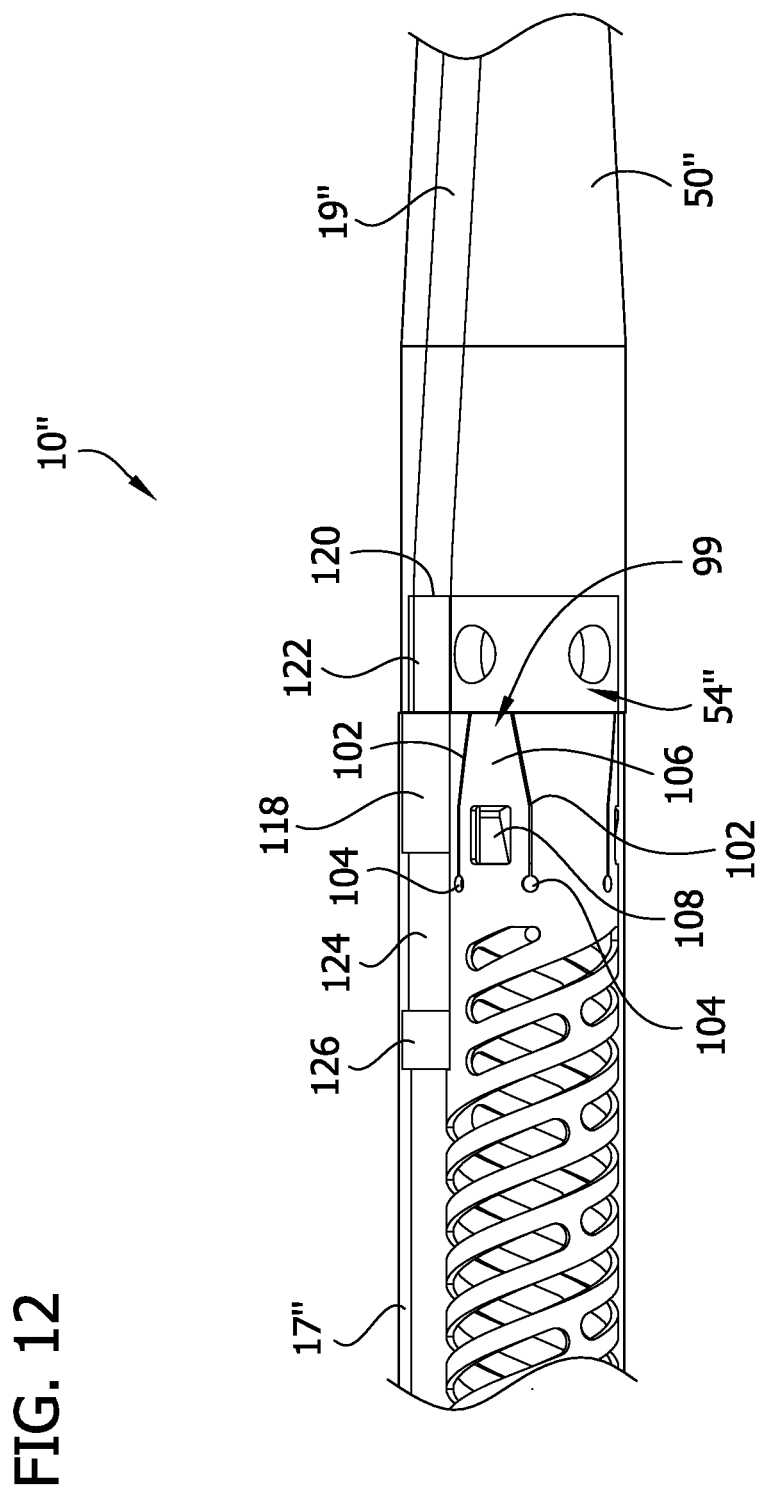
FIG. 12 is an illustration of a distal end of a catheter of another embodiment showing the catheter is a closed position and with a tissue containment chamber and distal end shown as transparent showing internal detail.
Figure 13:
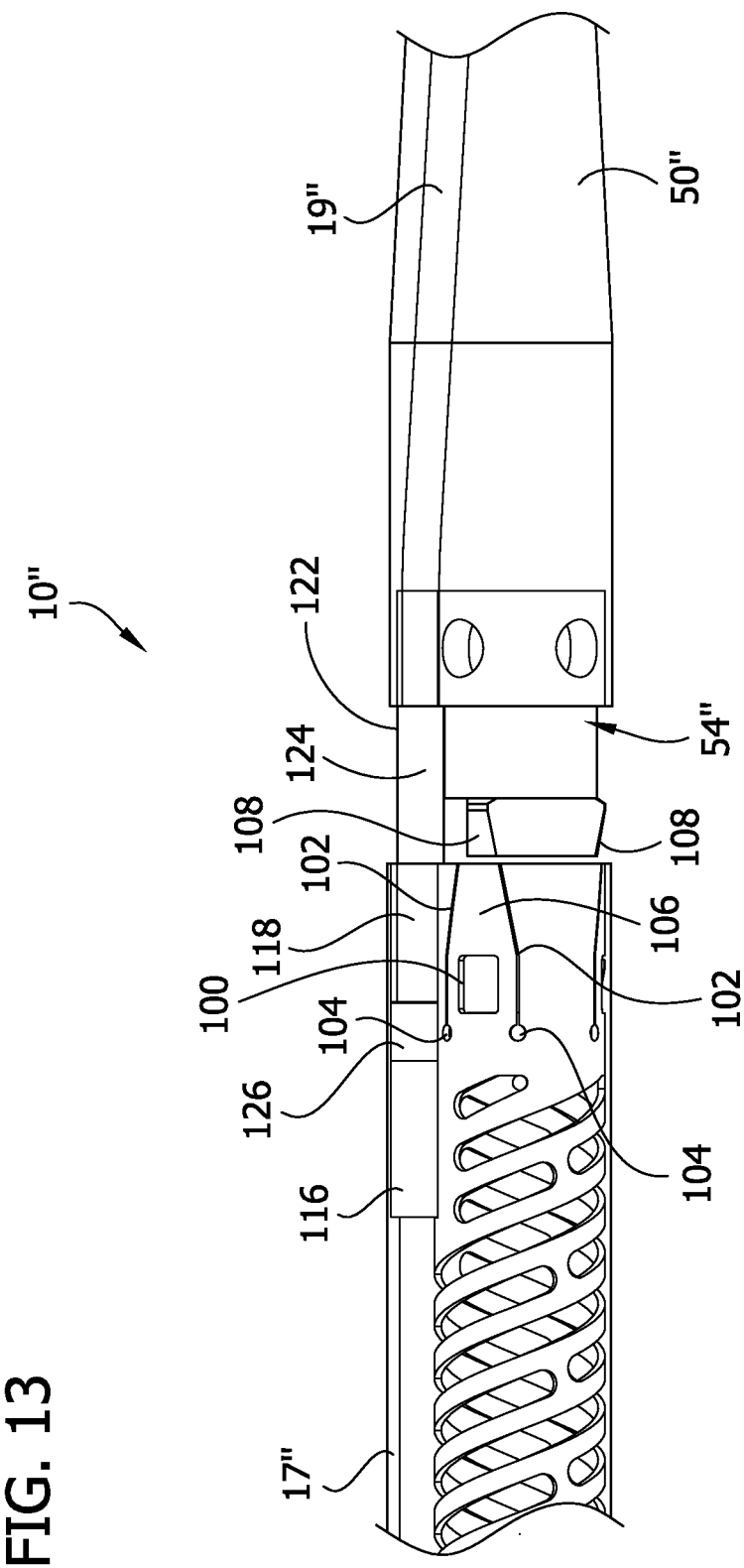
FIG. 13 is an illustration of the distal end of the catheter of FIG. 12 showing the catheter is an intermediate position.
Figure 14:
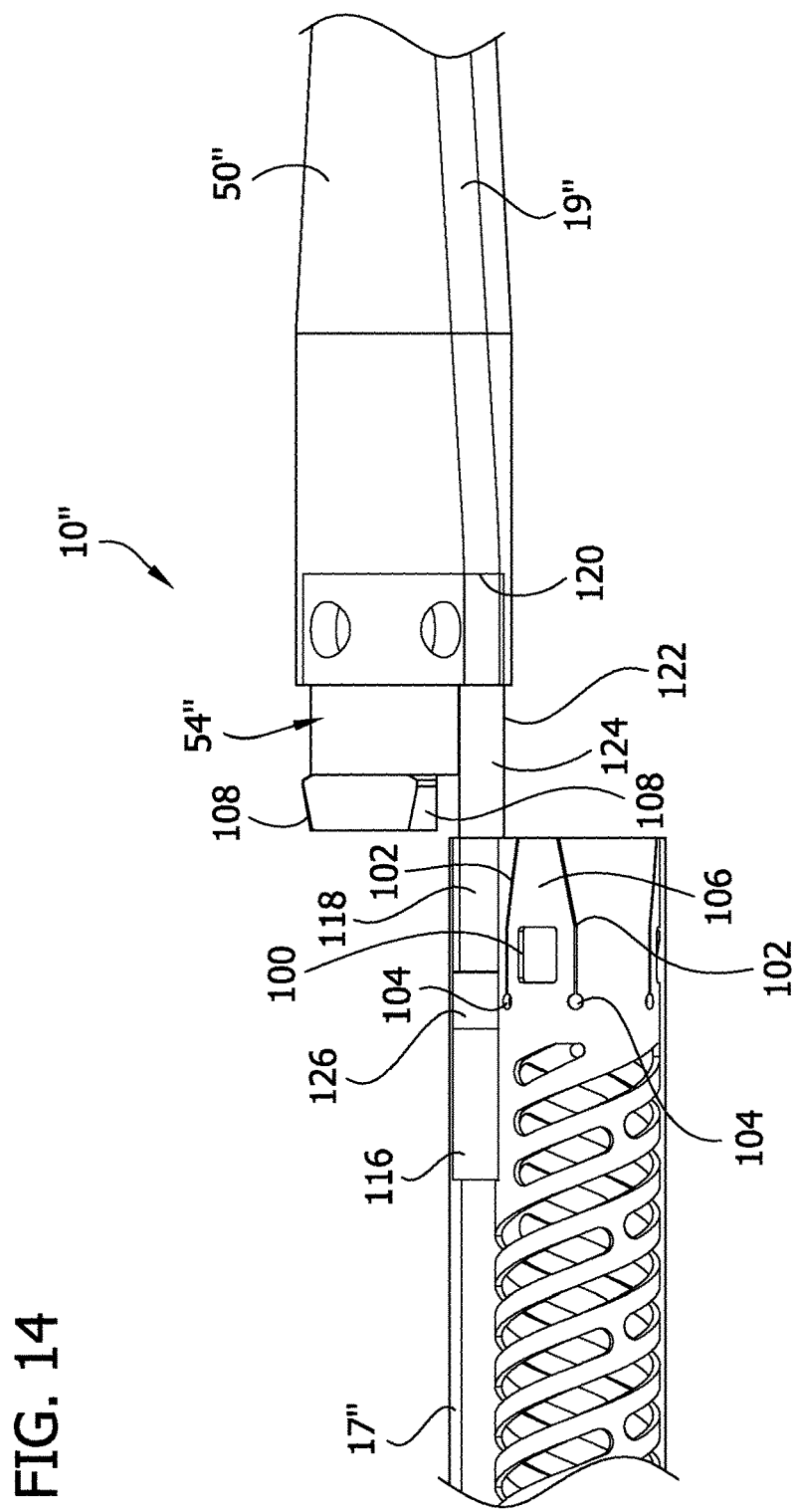
FIG. 14 is an illustration of the distal end of the catheter of FIG. 12 showing the catheter is an open position.

Referring to FIGS. 12-14, a catheter of another embodiment is illustrated generally at 10". A tissue-removing opening 52" (FIG. 14) in a tissue-containment chamber 17" of the catheter 10" allows removal of material stored in the chamber. The catheter 10" includes a closure component, generally indicated at 54", having a proximal end received in the tissue-removing opening 52" of the tissue-containment chamber 17" and a distal end attached to a proximal end of a distal tip component 50" such that movement of the distal tip component causes conjoint movement of the closure component. The distal tip component 50" and closure component 54" are movable to selectively open and close the tissue-removing opening 52" in the tissue-containment chamber 17". In the illustrated embodiment, the tissue-removing opening 52" is defined by a distal opening extending axially through the distal end of the tissue-containment chamber 17'. The tissue-removing opening 52" may be created in any other manner without departing from various aspects of the present disclosure.

The tissue-containment chamber 17" includes a plurality of catches, generally indicated at 99 (only one is shown), near the distal end of the tissue-containment chamber. Each catch 99 is generally in the form of a deflectable cantilever snap-fit arm defining an opening 100 therein. The openings 100 are spaced circumferentially around the tissue-containment chamber 17" and each opening is spaced from a distal edge of the tissue-containment chamber. A plurality of narrow slits 102 are formed in the distal end to the tissue-containment chamber 17" and spaced circumferentially around the tissue-containment chamber to form the catches 99. Each slit 102 extends from the distal edge of the tissue-containment chamber 17" to a widened base 104. A pair of slits 102 is associated with each catch 99. As illustrated, each pair of slits 100 is disposed on opposite circumferential sides of a catch 100. Each catch 99 is resiliently deflectable or flexible radially outward when engaged by the closure component 54" as will be explained in greater detail below.

Figure 15:
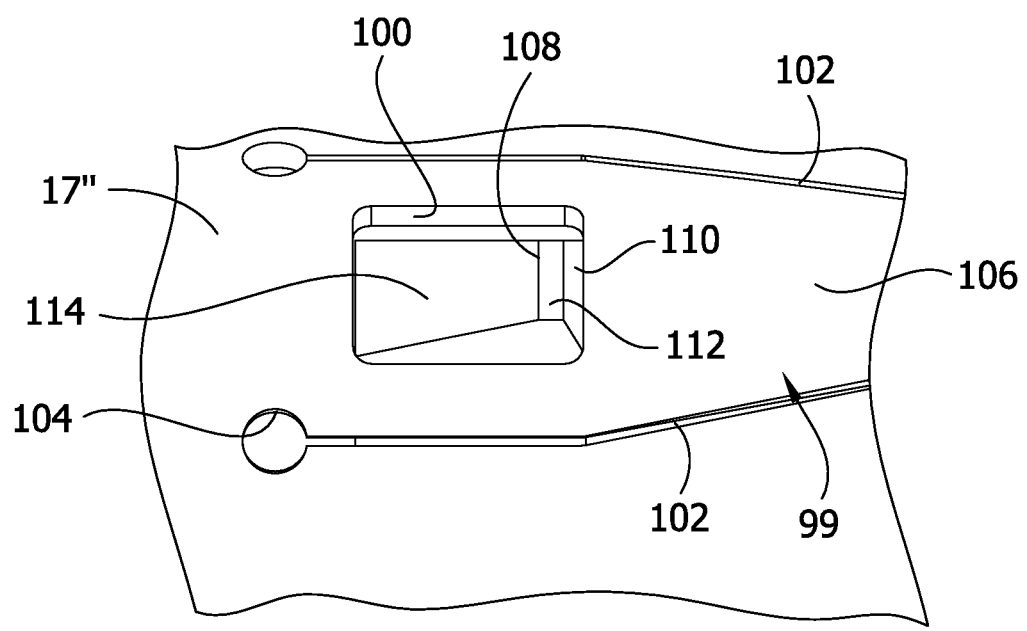
FIG. 15 is an enlarged fragmentary view of a distal end of a tissue-containment chamber of the catheter of FIG. 12.

The closure component 54" includes a plurality of hooks 108 disposed adjacent a proximal end of the closure component. In the illustrated embodiment, the hooks 108 are connected to one another and are part of a single hook base unit 109. When the proximal end of the closure component 54" is fully received in the distal end of the tissue-containment chamber 17", the hooks 108 are captured within the openings 100 of the respective catches 99 to secure the distal tip component 50" and closure component 54" to the tissue-containment chamber 17". Referring to FIG. 15, each hook 108 includes a first ramp surface 110, a second ramp surface 112, and a third ramp surface 114. The first ramp surface 110 extends upwards from a leading edge of the ramp 108 at an angle to the second ramp surface 112. The second ramp surface extends from the first ramp surface 110 to the third ramp surface 114 generally along a plane parallel to an outer surface of the tissue-containment chamber 17". The third ramp surface 114 extends downward from the second ramp surface 112 toward a trailing edge of the ramp 108. As explained below, the structure of the hooks 108 allows for releasable locking of the closure component 54" in the tissue-containment chamber 17".

A first tube lumen 116 is disposed on the tissue-containment chamber 17". The first tube lumen 116 extends from a distal edge of the tissue-containment chamber 17" to a location proximal to the distal edge of the tissue-containment chamber. A first tube 118 is fixedly disposed in first the tube lumen 116 generally at a distal end of the first tube lumen. A second tube lumen 120 is disposed on the closure component 54". The second tube lumen 120 extends from a proximal edge of the closure component 54" to a location distal to the proximal edge of the closure component. A second tube 122 is fixedly disposed in the second tube lumen 120 and extends into the first tube lumen 116 in the tissue-containment chamber 17" and through the first tube 118 in the first tube lumen. The second tube 122 comprises a first diameter portion 124 sized to be received in the first tube 118 and slide within the first tube, and a second diameter portion 126 wider than the first diameter portion. The second diameter portion 126 is sized to abut the first tube 118 when the second hollow tube 122 is slid distally relative to the first tube. This configuration limits movement of the distal tip component 50" and closure component 54" away from the tissue-containment chamber 17" and allows rotation of the distal tip component and closure component relative to the tissue-containment chamber as will be explained in greater detail below. The tubes 118, 122 may be fixedly disposed in the lumens 116, 120 by any suitable means such as welding, brazing or adhesive. Moreover, the lumens 116, 120 may be omitted without departing from the scope of the present invention. The first and second diameter portions 124, 126 of the second tube 122 may be formed separately and attached to each other by any suitable means such as welding, brazing, or adhesive. Alternatively, the first and second diameter portion 124, 126 can be formed integrally. The first and second tubes 118, 122 are aligned with the proximal and distal guide wire lumen portions 19a, 19b, respectively, to partially define the guide wire lumen 19". A guide wire (not shown) is insertable through the guide wire lumen 19", including the first and second tubes 118, 122, respectively.

In the closed position, the closure component 54" is received in the tissue-removing opening 52" of the tissue-containment chamber 17" and the hooks 108 on the closure component are captured in the openings 100 of the catches 99 to secure the distal tip component 50" and closure component to the tissue-containment chamber. To open the tissue-removing opening 52", an axial pulling force in a distal direction is applied to the distal tip component 50". A sufficient amount of force causes the closure component 54" to move distally and an inner surface of the catches 99 to ride up the first ramp surfaces 110 of the hooks 108. As the catches 99 ride up the first hook surfaces 110, the catches resiliently deflect outward and away from the hooks 108 providing clearance for the closure component 54" to continue its distal movement. Continued distal movement of the closure component 54" will cause the inner surfaces of the catches 99 to reach the second ramp surfaces 112 and then ride down the third ramp surfaces 114 freeing the hooks from the openings 100. Once the hooks 108 are free from the openings 100 the closure component 54" and hooks 108 can be pulled completely out of the tissue-containment chamber 17". Distal movement of the distal tip component 50" and closure component 54" is stopped when the second diameter portion 126 of the second hollow tube 122 engages the first hollow tube 118.

After removing the closure component 54" from the tissue-containment chamber 17", the distal tip component 50" and closure component 54" are rotated, whereby the second tube 122 rotates about an axis of the first tube 118, until the tissue-removing open is open. For instance, the distal tip component 50" and closure component 54" can be rotated about 180 degrees about the first tube 118 to open the tissue-removing opening 52". Other degrees of rotation are also envisioned. Thus, the distal tip component 50" and closure component 54" rotate about an axis that is radially offset from a longitudinal axis of the tissue-containment chamber 17". In the illustrated embodiment, the rotation is around an axis coincident with at least a portion of the guide wire lumen 19". As a result, the guide wire (not shown) and guide wire lumen 19" are not placed in shear or deformed by rotation of the distal tip component 50" and closure component 54".

To close the tissue-removing opening 52", the distal tip component 50" and closure component 54" are rotated back into alignment with the tissue-removing opening and pushed proximally until the hooks 108 on the closure component are captured by the openings 100 of the catches 99, thereby locking the distal tip component 50" and closure component to the tissue-containment chamber 17". As the closure component 54" is pushed proximally into the tissue-containment chamber 17", the third ramp surfaces 114 of the hooks 108 engage interior surfaces of the catches 99. A sufficient amount of force causes the closure component 54" to move proximally and the inner surfaces of the catches 99 to ride up the third ramp surfaces 114 of the ramps 108. As the catches 99 ride up the third ramp surfaces 114, the catches resiliently deflect outward and away from the hooks 108 providing clearance for the closure component 54" to continue its proximal movement. Continued proximal movement of the closure component 54" will cause the inner surfaces of the catches 99 to reach the second ramp surfaces 112 and then ride down the first ramp surfaces 110 capturing the hooks 108 in the openings 100.

The catheter 10" of this embodiment is also capable of being cleaned without the use of a separate flush tool. By adjusting a packing stroke length of the catheter 10" it is possible to push any tissue in the tissue-containment chamber 17" out of the catheter 10" by pushing the tissue distally in the tissue-containment chamber. In this embodiment, a cutter driver (not shown) may operate in at least two settings for controlling the packing stroke of the cutter. For instance, the cutter driver may operate in a first setting for packing tissue while the tissue-removing opening 52" is closed and a second setting for expelling tissue from the catheter 10" when the tissue-removing opening is open. Because the tissue-removing opening 52" is aligned with the longitudinal axis of the tissue-containment chamber 17", the tissue can be removed from the catheter 10" by this operation alone. To further facilitate removing tissue from the catheter 10" in this manner, a distal end of the tissue-containment chamber 17" may have a tapered inner diameter to reduce friction between the packed tissue and the tissue-containment chamber.

Having described embodiments of the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a body lumen, the catheter comprising:
    an elongate body having proximal and distal ends;
    a tissue-removing element adjacent the distal end of the elongate body, the tissue-removing element configured to engage and remove tissue from the body lumen;
    a tissue-containment chamber adjacent the distal end of the elongate body and configured to receive tissue removed by the tissue-removing element, the tissue-containment chamber defining a chamber lumen and having a proximal end connected to the distal end portion of the elongate body, a distal end opposite the proximal end, a longitudinal axis extending between the proximal and distal ends, and a tissue-removing opening adjacent to and spaced apart from the distal end thereof;
    a closure component in the chamber lumen of the tissue-containment chamber, the closure component being slidable longitudinally in a distal direction within the chamber lumen from a closed position, in which the closure component inhibits removed tissue in the tissue-containment chamber from exiting through the tissue-removing opening, to an open position, in which the closure component allows removed tissue in the tissue-containment chamber to exit through the tissue-removing opening.

2. The tissue-removing catheter set forth in claim 1, further comprising a boss-and-groove connection connecting the closure component to the tissue-containment chamber.

3. The tissue-removing catheter set forth in claim 2, wherein the boss-and-groove connection includes a groove associated with the closure component and extending along the closure component, and a boss on the tissue-containment chamber and retained within and movable along the groove.

4. The tissue-removing catheter set forth in claim 3, wherein the groove is generally L-shaped with a long arm extending along the closure component and a short arm extending crosswise of the closure component.

5. The tissue-removing catheter set forth in claim 4, wherein the closure component is in a locked configuration and inhibited from sliding longitudinally within the chamber lumen when the boss is in the short arm of the L-shaped groove, and wherein the closure component is in an unlocked configuration and allowed to slide longitudinally within the chamber lumen when the boss is in the long arm of the L-shaped groove.

6. The tissue-removing catheter set forth in claim 5, wherein the distal end of the tissue-containment chamber defines a distal opening, wherein the closure component extends through the distal opening of the tissue-containment chamber and into the chamber lumen.

7. The tissue-removing catheter set forth in claim 6, further comprising a tip component defining a distal end of the tissue-removing catheter, wherein the tip component is connected to a distal end of the closure component.

8. The tissue-removing catheter set forth in claim 7, wherein the tip component is rotatable relative to the tissue-containment chamber to move the closure component between its locked and unlocked configurations.

9. The tissue-removing catheter set forth in claim 8, further comprising a first guide wire lumen on the tissue-containment chamber and a second guide wire lumen on the tip component, wherein the first and second guide wire lumens are aligned for receiving a guide wire therethrough when the closure component is in its locked configuration.

10. The tissue-removing catheter set forth in claim 9, wherein the first and second guide wire lumens are misaligned when the closure component is in its unlocked configuration.

11. The tissue-removing catheter set forth in claim 10, wherein the tip component is rotatable relative to the tissue-containment chamber to move the closure component from its locked configuration to its unlocked configuration when a guide wire is received in the first and second guide wire lumens.

12. The tissue-removing catheter set forth in claim 1, wherein the closure component is selectively lockable in the closed position to inhibit unintentional movement of the closure component to the open position, and wherein the closure component is selectively unlockable in the closed position to allow movement of the closure component to the open position.

13. The tissue-removing catheter set forth in claim 12, wherein the distal end of the tissue-containment chamber defines a distal opening, wherein the closure component extends through the distal opening of the tissue-containment chamber and into the chamber lumen.

14. The tissue-removing catheter set forth in claim 13, further comprising a tip component defining a distal end of the tissue-removing catheter, wherein the tip component is connected to a distal end of the closure component.

15. The tissue-removing catheter set forth in claim 14, wherein the tip component is rotatable relative to the tissue-containment chamber to selectively lock and unlock the closure component.

16. The tissue-removing catheter set forth in claim 14, further comprising a first guide wire lumen on the tissue-containment chamber and a second guide wire lumen on the tip component, wherein the tip component is rotatable relative to the tissue-containment chamber to selectively lock and unlock the closure component when a guide wire is received in the first and second guide wire lumens.

17. A method of cleaning a tissue-removing catheter, the method comprising:

inserting a tissue-removing catheter into a body lumen of a subject, the tissue-removing catheter including an elongate body having proximal and distal ends;

removing tissue from the body lumen by engaging the tissue with a tissue-removing element adjacent the distal end of the elongate body;

capturing the removed tissue from the body lumen in a tissue-containment chamber adjacent the distal end of the elongate body, wherein the tissue-containment chamber defines a chamber lumen and has a proximal end connected to the distal end portion of the elongate body, a distal end opposite the proximal end, a longitudinal axis extending between the proximal and distal ends, and a tissue-removing opening adjacent to and spaced apart from the distal end thereof, wherein a closure component in the chamber lumen of the tissue-containment chamber is in a closed position during said capturing the removed tissue to inhibit the removed tissue in the tissue-containment chamber from exiting through the tissue-removing opening;

removing the tissue-removing catheter from the body lumen of the subject after said removing tissue from the body lumen using the tissue-removing catheter and said capturing the removed tissue;

sliding, after said removing the tissue-removing catheter, the closure component longitudinally in a distal direction within the chamber lumen from the closed position to an the open position, in which the closure component allows removed tissue in the tissue-containment chamber to exit through the tissue-removing opening;

forcing the removed tissue in the tissue-containment outside the tissue-containment chamber through the tissue-removing opening when the closure component is in the open position.

18. The method of cleaning a tissue-removing catheter set forth in claim 17, further comprising rotating, after said removing the tissue-removing catheter and before said sliding the closure component longitudinally, the closure component relative to the tissue-containment chamber from a locked configuration to an unlocked configuration.

19. The method of cleaning a tissue-removing catheter set forth in claim 18, wherein said rotating the closure component comprises manually rotating a tip component connected to the closure component, wherein the tip component defines a distal end of the tissue-removing catheter.

20. The method of cleaning a tissue-removing catheter set forth in claim 17, wherein the steps of removing the tissue-removing catheter, sliding the closure component longitudinally within the chamber lumen, and forcing the removed tissue in the tissue-containment chamber through the tissue-removing opening are performed while the tissue-removing catheter is on a guide wire.

21. A tissue-removing catheter for removing tissue from a body lumen, the catheter comprising:

an elongate body having proximal and distal ends;

a tissue-removing element adjacent the distal end of the elongate body, the tissue-removing element configured to engage and remove tissue from the body lumen;

a tissue-containment chamber adjacent the distal end of the elongate body and configured to receive tissue removed by the tissue-removing element, the tissue-containment chamber defining a chamber lumen and having a proximal end connected to the distal end portion of the elongate body, a distal end opposite the proximal end, a longitudinal axis extending between the proximal and distal ends, and a tissue-removing opening adjacent to and spaced apart from the distal end thereof; and a closure component in the chamber lumen of the tissue-containment chamber, the closure component being slidable longitudinally within the chamber lumen between a closed position, in which the closure component inhibits removed tissue in the tissue-containment chamber from exiting through the tissue-removing opening, and an open position, in which the closure component allows removed tissue in the tissue-containment chamber to exit through the tissue-removing opening, wherein the closure component is selectively lockable in the closed position to inhibit unintentional movement of the closure component to the open position, and wherein the closure component is selectively unlockable in the closed position to allow movement of the closure component to the open position.

22. The tissue-removing catheter set forth in claim 21, wherein the distal end of the tissue-containment chamber defines a distal opening, wherein the closure component extends through the distal opening of the tissue-containment chamber and into the chamber lumen.

23. The tissue-removing catheter set forth in claim 22, further comprising a tip component defining a distal end of the tissue-removing catheter, wherein the tip component is connected to a distal end of the closure component.

24. The tissue-removing catheter set forth in claim 23, wherein the tip component is rotatable relative to the tissue-containment chamber to selectively lock and unlock the closure component.

* * * * *